US012631603B2

(12) United States Patent     (10) Patent No.:   US 12,631,603 B2

Koza et al.          (45) Date of Patent:    May 19, 2026

(54) SYSTEMS AND METHODS FOR TWO-DIMENSIONAL LIQUID CHROMATOGRAPHY USING SIZE EXCLUSION CHROMATOGRAPHY AS A FIRST DIMENSION

(71) Applicant: Waters Technologies Corporation, Milford, MA (US)

(72) Inventors: Stephan M. Koza, Lancaster, MA (US); Pamela Iraneta, Brighton, MA (US); Hua Yang, Hopkinton, MA (US)

(73) Assignee: Waters Technologies Corporation, Milford, MA (US)

( * ) Notice: Subject to any disclaimer, the term of this patent is extended or adjusted under 35 U.S.C. 154(b) by 219 days.

(21) Appl. No.: 17/335,539

(22) Filed: Jun. 1, 2021

(65) Prior Publication Data

US 2021/0382021 A1     Dec. 9, 2021

Related U.S. Application Data

(60) Provisional application No. 63/036,648, filed on Jun. 9, 2020.

(51) Int. Cl.
| | |
|---|---|
| *G01N 30/46* | (2006.01) |
| *B01D 15/34* | (2006.01) |
| *G01N 30/32* | (2006.01) |
| *G01N 30/72* | (2006.01) |
| *G01N 33/68* | (2006.01) |
| *G01N 30/02* | (2006.01) |

(52) U.S. Cl.
CPC ........... *G01N 30/468* (2013.01); *B01D 15/34* (2013.01); *G01N 30/32* (2013.01); *G01N 30/463* (2013.01); *G01N 30/7233* (2013.01);

*G01N 33/6848* (2013.01); *G01N 2030/027* (2013.01); *G01N 2030/324* (2013.01)

(58) Field of Classification Search
CPC .... G01N 30/468; G01N 30/32; G01N 30/463; G01N 30/7233; G01N 33/6848; G01N 2030/027; G01N 2030/324; B01D 15/34; B01D 15/1878; B01D 15/325; B01D 15/361
See application file for complete search history.

(56) References Cited

U.S. PATENT DOCUMENTS

| | | | | |
|---|---|---|---|---|
| 6,730,228 B2* | 5/2004 | Petro | ...................... | G01N 30/20 |
| | | | | 210/659 |
| 2003/0070988 A1* | 4/2003 | Petro | ................... | B01J 19/0046 |
| | | | | 210/656 |

(Continued)

OTHER PUBLICATIONS

Liu, Hongji, et al. "Multidimensional chromatography coupled to electrospray ionization time-of-flight mass spectrometry as an alternative to two-dimensional gels for the identification and analysis of complex mixtures of intact proteins." Journal of Chromatography B 782.1-2 (2002): 267-289. (Year: 2002).*

(Continued)

*Primary Examiner* — Brian R Gordon

(74) *Attorney, Agent, or Firm* — WOMBLE BOND DICKINSON (US) LLP; Deborah M. Vernon; John V. Forcier

(57) ABSTRACT

Described herein are systems and methods used for carrying out a two-dimensional liquid chromatography process using size exclusion chromatography as a first dimension.

22 Claims, 10 Drawing Sheets

(56) References Cited

U.S. PATENT DOCUMENTS

| | | | | |
|---|---|---|---|---|
| 2007/0023639 A1* | 2/2007 | Yamashita | .......... | G01N 30/463 |
| | | | | 250/288 |
| 2007/0295664 A1* | 12/2007 | Glatz | .................. | G01N 30/462 |
| | | | | 210/656 |
| 2008/0210614 A1* | 9/2008 | Gilar | ...................... | G01N 30/34 |
| | | | | 556/400 |
| 2010/0107742 A1* | 5/2010 | Liu | ......................... | G01N 30/34 |
| | | | | 73/61.56 |
| 2012/0305464 A1* | 12/2012 | Cormier | ................. | G01N 30/20 |
| | | | | 137/1 |
| 2015/0122655 A1* | 5/2015 | Choikhet | ............. | G01N 30/465 |
| | | | | 204/600 |
| 2015/0355147 A1* | 12/2015 | Bellinzoni | ............ | G01N 30/74 |
| | | | | 506/12 |
| 2016/0054273 A1* | 2/2016 | Hyung | ................. | G01N 30/463 |
| | | | | 73/61.56 |
| 2016/0238573 A1* | 8/2016 | Venkatramani | ...... | B01D 15/325 |
| 2016/0349220 A1* | 12/2016 | Laustsen | ................ | G01N 30/88 |
| 2017/0010243 A1* | 1/2017 | Gaita | ..................... | G01N 30/78 |
| 2017/0209812 A1* | 7/2017 | Dlugasch | .............. | G01N 30/16 |

| | | | | |
|---|---|---|---|---|
| 2019/0275275 A1* | 9/2019 | Brown | ................... | B01J 20/262 |
| 2020/0011841 A1* | 1/2020 | Eriksson | ................ | G01N 30/20 |
| 2021/0223216 A1* | 7/2021 | Stoll | .................... | G01N 30/463 |
| 2022/0050091 A1* | 2/2022 | Sugiyama | ............. | G01N 30/46 |
| 2022/0137061 A1* | 5/2022 | Wu | ........................ | G01N 30/06 |
| | | | | 435/7.1 |
| 2022/0233798 A1* | 7/2022 | Brown | ................. | A61M 16/01 |

OTHER PUBLICATIONS

Goyon et al. "Extending the limits of size exclusion chromatography: Simultaneous separation of free payloads and related species from antibody drug conjugates and their aggregates." J. Chromatogr. A. 1539(2018): 19-29.

Li et al. "A size exlucsion-reversed phase two dimensional-liquid chromatography methodology for stability and small molecule related species in antibody drug conjugates." J. Chromatogr. A. 1393(2015): 81-88.

Schneider "Online 2D-LC Characterization of Monoclonal Antibodies with Size Exclusion and Weak Cation Exchange Chromatography." Agilent Technologies Application Note. (2016).

* cited by examiner

SEC mobile phase: 25 mM sodium phosphate with 400 mM sodium chloride, pH 7.2

IEX mobile phases: IonHance CX-MS pH buffer concentrates, 10 x dilution

148708

148229

148225

148230

148388

148208

RAW SPECTRA DECONVOLUTED SPECTRA

SYSTEMS AND METHODS FOR TWO-DIMENSIONAL LIQUID CHROMATOGRAPHY USING SIZE EXCLUSION CHROMATOGRAPHY AS A FIRST DIMENSION

FIELD OF DISCLOSURE

This disclosure relates generally to two-dimensional liquid chromatography, and in particular, to systems and methods for carrying out the two-dimensional liquid chromatography process using size exclusion chromatography as a first dimension.

BACKGROUND

Generally, the characterization of biotherapeutics is challenging due to the complexity of the drugs. Two-dimensional liquid chromatography (2D-LC) and two-dimensional liquid chromatography and mass spectrometry (2D-LC-MS) have been used to obtain such information; however, two-dimensional system suffer significant drawbacks because of their complexity and the fact that these systems are not intuitive to set-up, requiring expertise or extensive training.

Size exclusion chromatography (SEC) is a widely used chromatographic technique for separating proteins based on their sizes or hydrodynamic radii. This separation method is usually an isocratic process, and the separation mechanism is based on different size molecules spending different amounts of time diffusing in and out of the pores on the packing material. Larger molecules are harder to get into the pores, while smaller molecules are easier, resulting in larger molecules being eluted earlier than smaller molecules.

FIG. 1 depicts one example of a known 2D-LC system for analyzing biopharmaceuticals. As can be seen, the system is highly complex with many additional components (e.g., loops and traps), each of which can be a point of failure (e.g., leaks, contamination) in the system.

Accordingly, there is a need for a system that is simple and intuitive to configure and operate.

SUMMARY

The invention is directed to a unique and simple way to configure and operate a 2D-LC-MS system using SEC as the first dimension. Generally, the systems and methods described herein can help to obtain charge variant information of large molecules, such as mAbs, with different size species under native conditions.

In one aspect, the disclosure is related to a system for performing a two-dimensional liquid chromatography process. The system includes a first dimension including a size exclusion chromatography as a first analytical device, a first pump in fluid communication with the size exclusion chromatography first analytical device and configured to deliver a sample thereto, a second dimension including a second analytical device, a second pump in fluid communication with the second analytical device and configured to deliver a diluent to an eluent of the first analytical device prior to introduction of the eluent to the second analytical device, and a mechanism configured to regulate the flow of the eluent of the first dimension.

In various embodiments of the foregoing aspect, the mechanism is a two-position, six-port valve arrangement in fluid communication with the first dimension and the second dimension, wherein the valve is configured to direct an output of the first dimension (also referred to herein as the eluent) to either the second dimension or an alternative output. However, other mechanisms for regulating flow are contemplated and considered within the scope of the invention. The alternative output may be in fluid communication with at least one of a waste receptacle, a holding tank, or an additional analytical device, such as those disclosed herein. Additionally, the system may include a tee in fluid communication with the second pump and the second dimension and configured to merge the output of the first dimension with the diluent. In certain embodiments, the second analytical device may be at least one of an ion exchange device, a hydrophobic interaction chromatography device, a purification device, a reverse phase chromatography device, a mass spectrometer, or a combination thereof. The second dimension may include a third analytical device, such as at least one of an ion exchange device, a hydrophobic interaction chromatography device, a purification device, a reverse phase chromatography device, a mass spectrometer or a combination thereof. The second analytical device may be oriented in parallel with the third analytical device and the second dimension may further include a valve configured to direct the output of the first dimension to either the second analytical device or the third analytical device. In some embodiments, the second analytical device is oriented in series with the third analytical device. The system may also include an optical detector disposed downstream of the first dimension and/or one or more sensors for monitoring operation of the system and providing feedback thereof.

In another aspect, the invention relates to a method of performing a two-dimensional liquid chromatography process. The method includes the steps of introducing a sample to a first dimensional process, wherein the first dimensional process utilizes a size exclusion chromatography device as a first analytical device; directing an eluent (i.e., output) of the first dimensional process to a second dimensional process, wherein the second dimensional process utilizes a second analytical device; regulating a flow of the eluent from the first dimensional process to the second dimensional process; introducing a diluent to the second dimensional process with the eluent from the first dimensional process; and starting the second dimensional process.

In various embodiments of the foregoing aspect, the step of regulating the flow of the eluent comprises stopping the flow of the eluent from the first dimensional process to the second dimensional process. The steps of directing the eluent of the first dimensional process and regulating a flow of the eluent to the second dimensional process may be carried out via a two-position, six-port valve arrangement in fluid communication with the first dimensional process and the second dimensional process. A first position of the valve is configured to direct the eluent of the first dimensional process to the second dimensional process and a second position of the valve is configured to direct the eluent of the first dimensional process to an alternative output. However, other mechanisms for regulating the flow are contemplated and considered within the scope of the invention. The step of introducing the diluent to the second dimensional process may include using a tee to perform an at column dilution of the eluent from the first dimensional process into an inlet of the second dimensional process. The first dimensional process flow may be stopped repeatedly (essentially an unlimited number of cycles) (or fractions of eluent regulated) for a total time of 1 to 4 hours (analyte dependent), and more preferably for 1 hour or less without a significant loss of resolution. In some embodiments, the flow of the eluent is stopped for the time taken to complete the second dimensional process, wherein a protein of interest in the sample has a mass of greater than 100 Da, preferably greater than 20 kDa, and more preferably 100 kDa. Generally, the time of the stoppage may vary to suit a particular application (e.g., molecular weights, particular proteins of interest, etc.).

In additional embodiments, the flow of the eluent from the first dimension is stopped or directed to waste after a desired fraction of the protein sample has been directed to the second dimensional process. The volume of the desired sample will vary to suit a particular application (e.g., protein of interest, size of the column, etc.). The method may also include the step of restarting the flow of the eluent of the first dimensional process to direct a next desired fraction of the protein sample to the second dimensional process after completion of the second dimensional process for the previous desired fraction of the protein sample. In most cases, the tracking of the protein analytes can be based solely on a previously determined elution volume. The method may also include the step of directing an output of the second analytical device to a third analytical device. In some embodiments, the step of introducing the sample includes injecting multiple samples into the first dimensional process. The process is isocratic. In additional embodiments, the process is carried out with the sample at a low temperature, for example, less than 30° C. Additionally, the process may be carried out without holding the output of the first dimensional process, such as with the use of traps, holding receptacles, or loops of tubing.

Still other aspects, embodiments, and advantages of these exemplary aspects and embodiments, are discussed in detail below. Moreover, it is to be understood that both the foregoing information and the following detailed description are merely illustrative examples of various aspects and embodiments, and are intended to provide an overview or framework for understanding the nature and character of the claimed aspects and embodiments. Accordingly, these and other objects, along with advantages and features of the present disclosure herein disclosed, will become apparent through reference to the following description and the accompanying drawings. Furthermore, it is to be understood that the features of the various embodiments described herein are not mutually exclusive and may exist in various combinations and permutations.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the disclosure and are not intended as a definition of the limits of the disclosure. For purposes of clarity, not every component may be labeled in every drawing. In the following description, various embodiments of the present disclosure are described with reference to the following drawings, in which.

DETAILED DESCRIPTION

Figure 1:
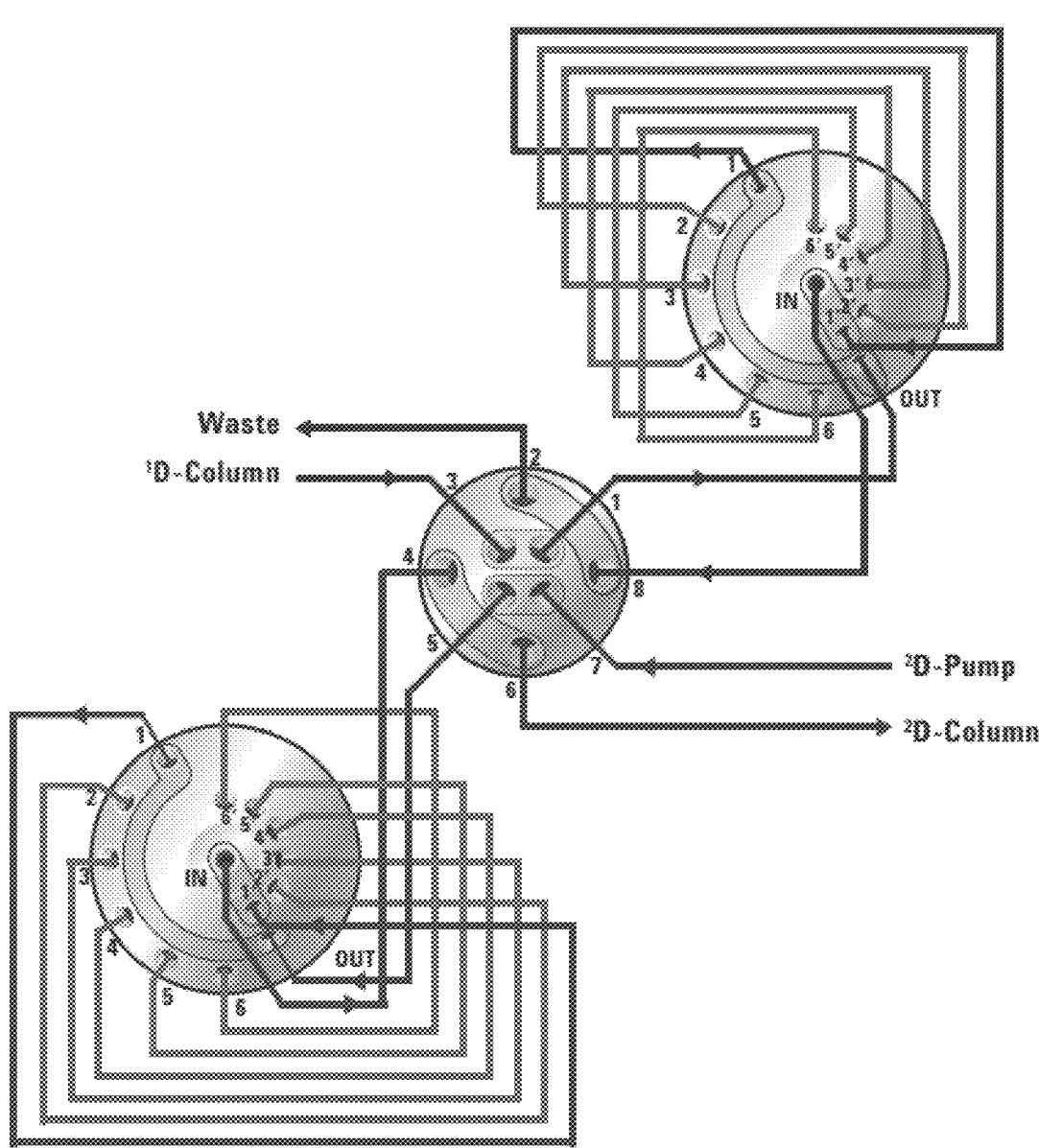
FIG. 1 is a schematic view of an existing 2D-LC system.

Reference will now be made to the exemplary embodiments illustrated in the drawings, and specific language will be used here to describe the same. It will nevertheless be understood that no limitation of the scope of the disclosure is thereby intended. Alterations and further modifications of the inventive features illustrated herein, and additional applications of the principles of the disclosure as illustrated herein, which would occur to one skilled in the relevant art and having possession of this disclosure, are to be considered within the scope of the disclosure.

Figure 2A:
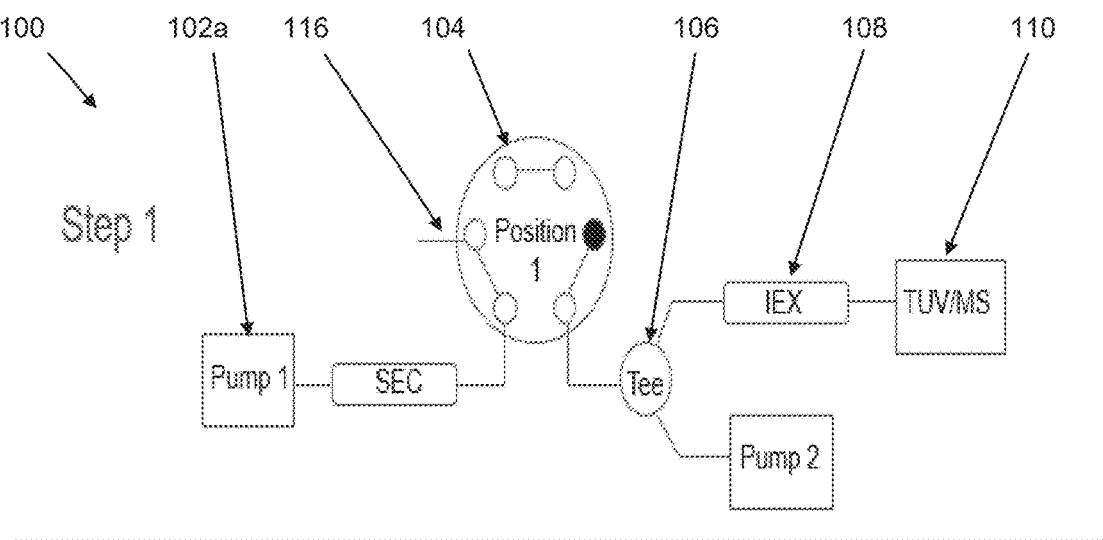
FIG. 2A is a schematic view depicting an arrangement of components within a 2D-LC system during various stages of the corresponding process in accordance with one or more embodiments of the disclosure.
Figure 2A:
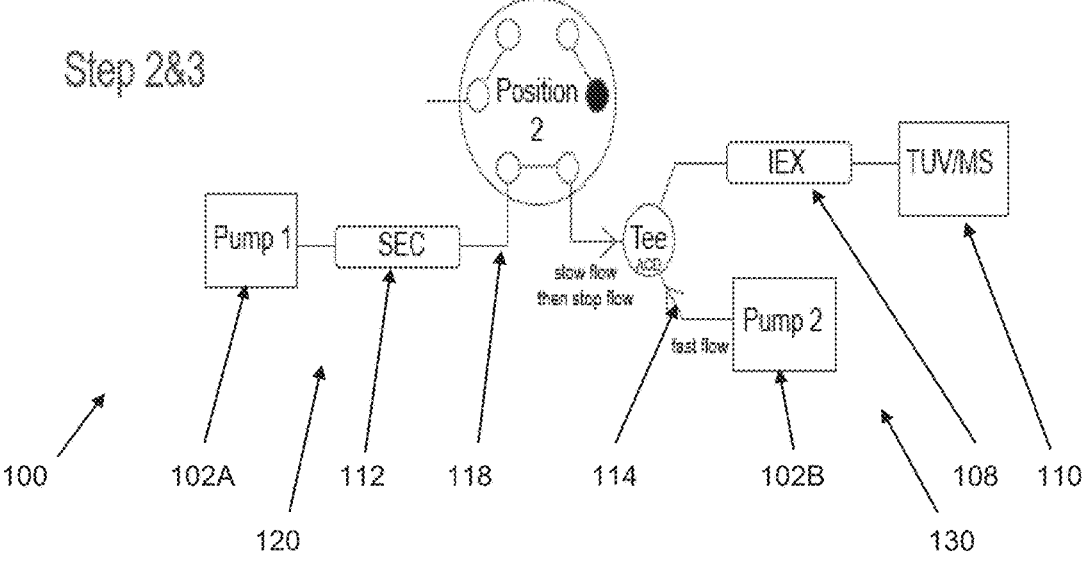

FIG. 2A illustrates one embodiment of a 2D LC MS system 100. There are two pumps 102a, 102b for the system 100, a first pump 102a for the first dimension 120 and a second pump 102b for the second dimension 130. The first pump 102a is in fluid communication with a source of a sample for analysis (not shown) and a SEC column 112 to provide the sample thereto. The second pump 102b is in fluid communication with a source of a diluent (not shown) and an analytical device 108, such as an ion exchange device, a hydrophobic interaction chromatography (HIC) device, a purification device, a reverse phase chromatography device, or a mass spectrometer, to provide the diluent to the column of the analytical device 108. In the exemplary system depicted in FIG. 2, the analytical device is an ion exchange device (IEX). In certain embodiments, the second dimension can utilize hydrophobic interaction chromatography (HIC).

The system 100 also includes a six-port, two-position valve 104 that is used to switch an output flow from the SEC column 112 to either an auxiliary output 116 or the second dimension 130. The auxiliary output 116 can be directed to, for example, a waste receptacle, a holding tank, or an additional analytical device to suit a particular application. A tee 106 is provided before the second dimension 130 for at column dilution (ACD) so as to achieve initial conditions for the second dimension separation. Generally, the tee 106 is in fluid communication with the second pump 102*b* and the analytical device 108 so as to merge the output 118 of the first dimension 120 with the diluent 114. In some embodiments, an additional valve (not shown) may be provided; however, one of the valves on the column manager may be configured for this process. Additional analytical devices 110 may be added downstream of the first analytical device 108, such as a mass spectrometer. No additional components are required; such as trap columns or loops. In some embodiments, certain instrumentation can be included; such as those used for temperature, pressure, and/or flow measurement. In various embodiments, the additional analytical device 110 may include an optical detector, such as a photodiode array (PDA), a tunable ultraviolet (TUV), an evaporative light scattering (ELS), or a fluorescence (FLR) type configured to monitor the peaks to be collected after the SEC separation.

The system 100 of FIG. 2A will be operated in a stop-flow manner (see the experimental data discussed in greater detail below). To begin, the sample flow is provided to the SEC column 112 as described above. During the SEC separation, the output flow 118 can be stopped when a certain fraction of the sample is sent to the second dimension 130 for analysis, where the flow is diverted to the auxiliary outlet 116. The flow 118 can be restarted to continue the first dimension separation. Specifically, at Step 1, the first dimension SEC separation is carried out; at Step 2, the SEC fraction (output flow 118) is sent to the second dimension, in this case IEX with At Column Dilution (ACD); and at Step 3, the SEC output flow 118 is stopped (e.g., diverted via valve 106) and the IEX process started. After the second dimension separation is completed, the SEC flow 118 can be re-started to produce another fraction to be sent to the second dimension. Alternatively or additionally, a user may enrich one peak on the IEX column by injecting multiple samples into the SEC column, sending the same fraction to the IEX column, and analyzing the fraction at once. In some embodiments, multiple IEX columns can be used with column selection for multiple peaks or samples.

Figure 2B:
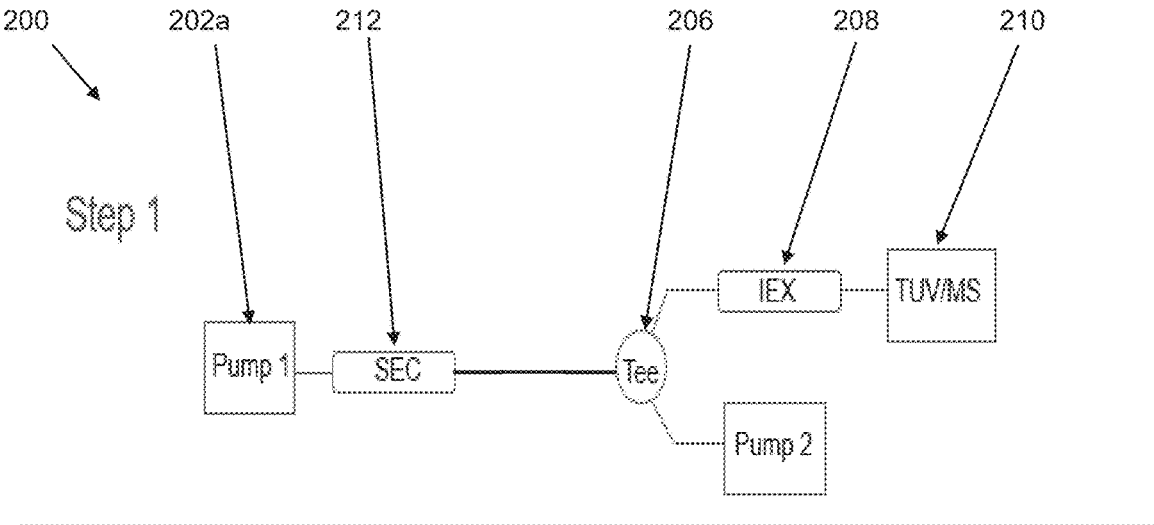
FIG. 2B is a schematic view depicting an alternative arrangement of components within a 2D-LC system during various stages of the corresponding process in accordance with one or more embodiments of the disclosure.
Figure 2B:
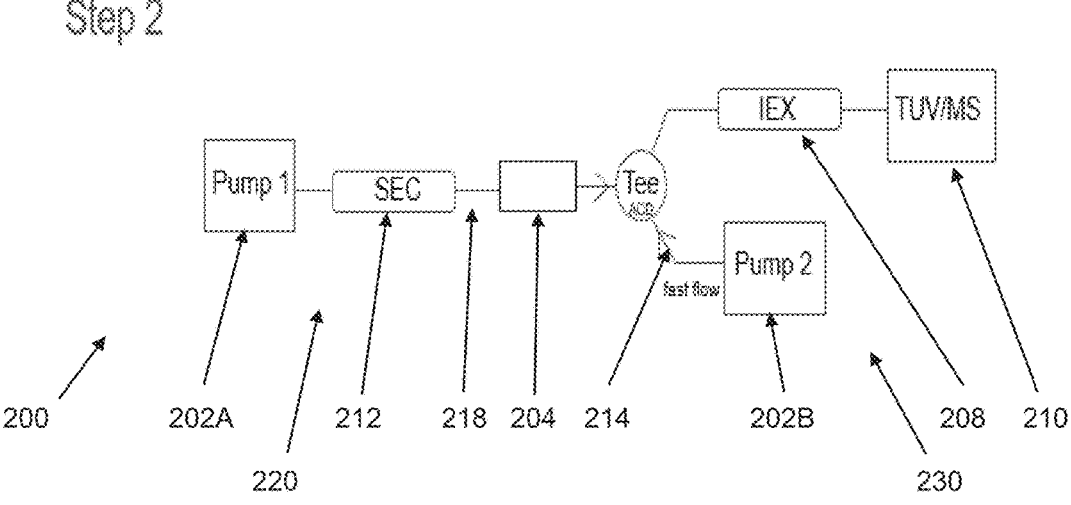

FIG. 2B depicts an alternative system 200 that is substantially similar to the system 100 of FIG. 2A insofar as it includes a first dimensional subsystem 220 and a second dimension subsystem 230, along with two pumps 202*a*, 202*b*, a SEC column 212, and various analytical devices 208, 210, as described above. The system 200 of FIG. 2B can also be operated in a similar matter to the system 100 of FIG. 2A; however, without the use of the valve 104. The system 200 may use a mechanism 204 to regulate the flow of the output from the first dimension to the second dimension. In some embodiments, the mechanism 204 can be valve arrangement as described above or it can be a control circuit (e.g., a switch) that turns the first pump 202*a* on and off for desired periods of time that would correlate to specific volumes of the sample delivered to the first dimension 220. In some embodiments, the flow from the first dimension can be stopped by starting the second pump 202*b* whose counter flow would impede flow from the first dimension, for example, via the use of check valves or other principles of fluid dynamics in the system's plumbing.

In various case studies, Applicant has used reverse phase (RP) chromatography and IEX for the second dimension, respectively. By using the inventive this 2D LC MS setup, useful mass information has been obtained that could not have been obtained using only one-dimensional SEC.

Generally, the diffusion coefficient of large proteins, such as monoclonal antibodies (mAbs), is on the order of $10^{-7}$ cm$^2$/s, which is approximately one order of magnitude lower than that of small molecules, such as uracil. As a result, the large molecules will move much slower than the small molecules in a given space. Due to the low diffusivity of large molecules, when flow is stopped in SEC, the large molecules will not diffuse far enough to cause bandspreading. In addition, it is possible that when the flow is stopped, the large molecules are more likely to diffuse in and out of the pores of nearby particles. This would result in even shorter distances the large molecules would diffuse away from their initial position. To test this hypothesis, a series of experiments were conducted where the flow was stopped for various amount of time and started again to separate the SEC standard mix.

Figure 3A:
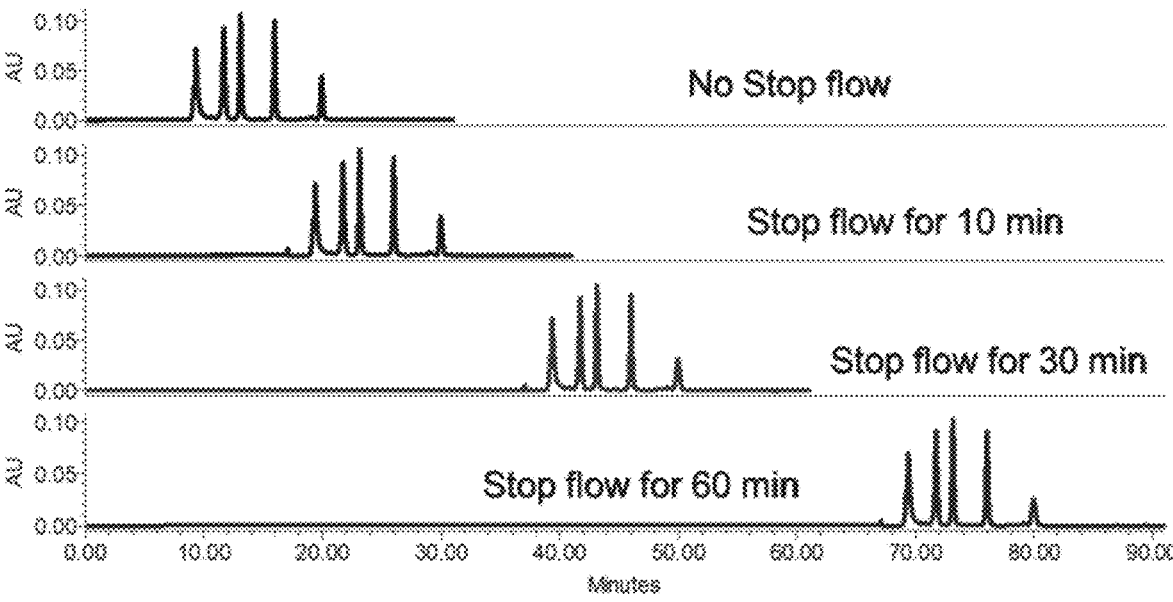
FIG. 3A is a graphical representation of the results of a stop flow experiment with SEC using a MW protein standard in accordance with one or more embodiments of the disclosure.
Figure 3B:
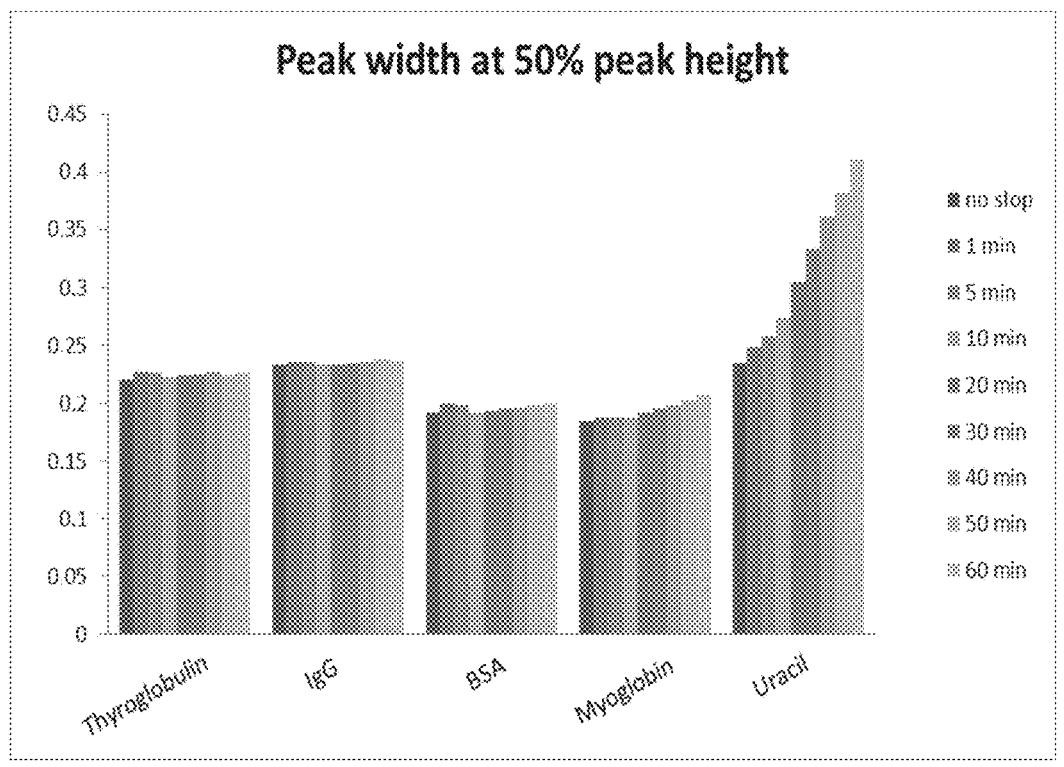
FIG. 3B is a graphical representation depicting one variable related to the effect of the length of the stopped flow generated via a process in accordance with one or more embodiments of the disclosure.
Figure 3C:
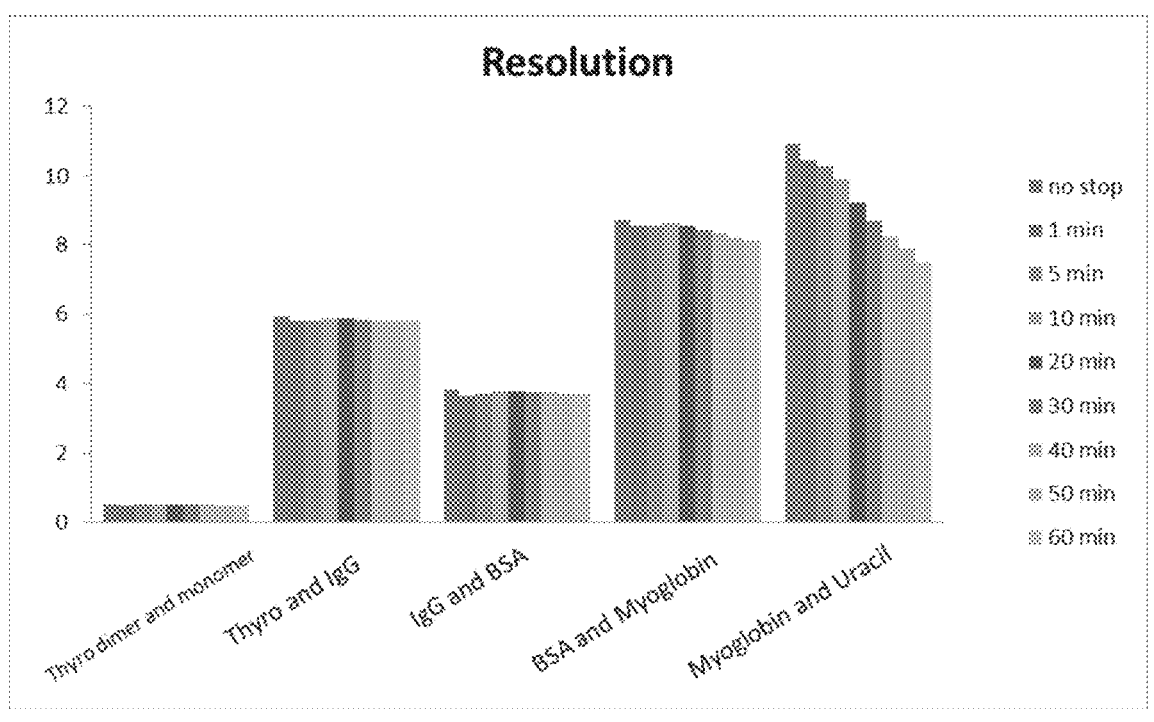
FIG. 3C is a graphical representation depicting another variable related to the effect of the length of the stopped flow generated via a process in accordance with one or more embodiments of the disclosure.

FIG. 3A depicts representative chromatograms for the stop-flow experiments, where the flow was stopped for 10 minutes, 30 minutes, and 60 minutes, as compared to no flow stoppage. As can be seen, the separation of the protein standards did not change significantly. FIGS. 3B and 3C represent the effect of the length of the flow stoppages on the separations. FIG. 3B depicts the peak widths at 50% peak height of individual proteins in the protein standard mix at no stopping of the flow to stops of 1 minute, 5 minutes, 10 minutes, 20 minutes, 30 minutes 40 minutes, 50 minutes, and 60 minutes, while FIG. 3C depicts the corresponding resolution. For large proteins, such as thyroglobulin (MW=660 kDa), Immunoglobulin G (IgG) (MW=150 kDa) and bovine serum albumin (BSA) (MW=67 kDa), the peak width did not change significantly even when the flow was stopped for 60 minutes. However, for small molecules, such as uracil (MW=112 Da), the peak width increased even when the flow was stopped for only 1 minute. For small proteins like myoglobin, the peak width started to increase when the flow was stopped for more than 20 min. These results show that bandspreading is minimal for large proteins, likely due to low diffusivity of the large molecules.

Figure 4:
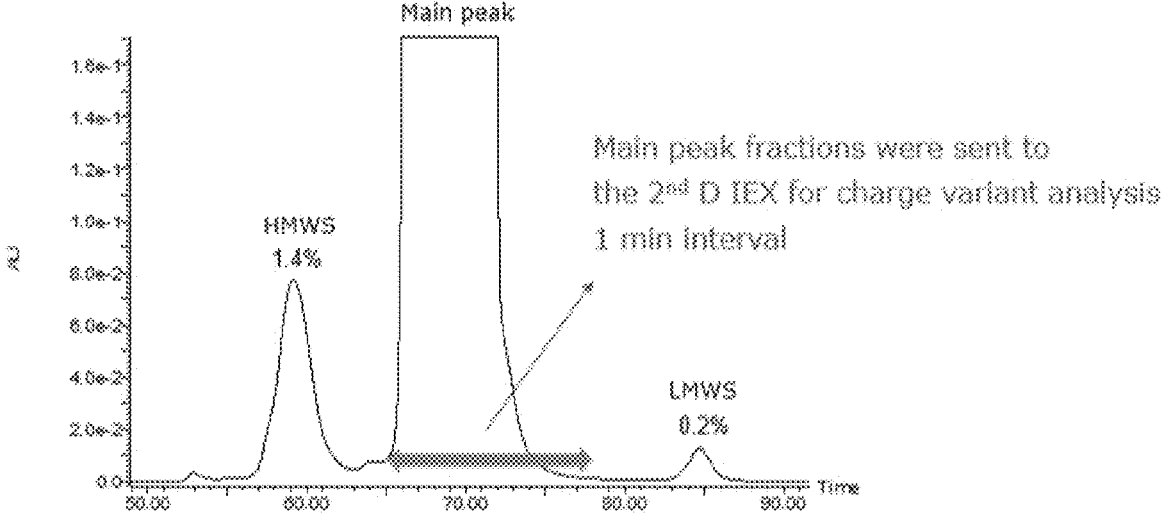
FIG. 4 is a graphical representation of the results of a first dimension (1D) SEC of trastuzumab generated via a process in accordance with one or more embodiments of the disclosure.

FIG. 4 depicts the results of a first dimensional process using SEC of trastuzumab, as generated by use of the systems described herein. The process was carried out with a mobile phase having 25 mM sodium phosphate with 400 mM sodium chloride at a pH of 7.2. The main peak fractions were sent to the second dimensional process using IEX.

Figure 5:
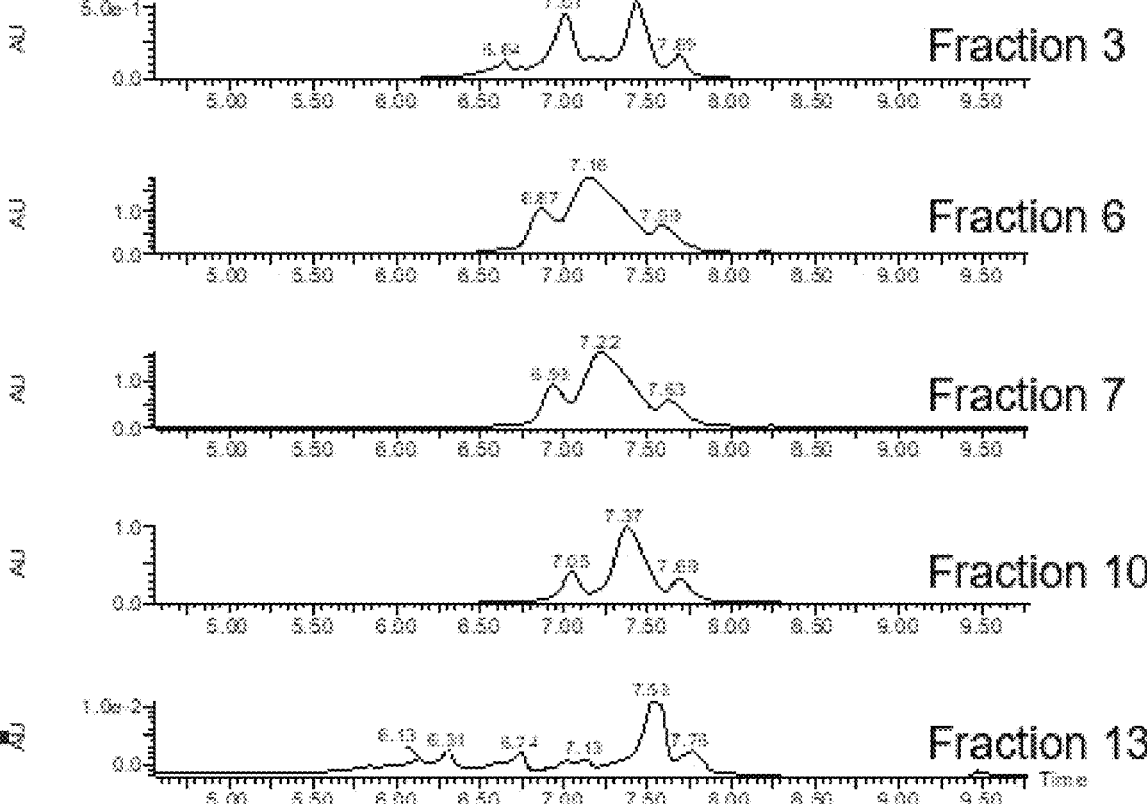
FIG. 5 is a graphical representation of the charge variant profiling across 1D SEC main peak by second dimension (2D) ion exchange (IEX) generated via a process in accordance with one or more embodiments of the disclosure.

FIG. 5 depicts the charge variant profiling across the first dimension SEC main peak fractions by second dimension IEX generated by use of the systems described herein. The graph shows the charge variances of various fractions from the first dimensional separations, where the output of the first dimension was processed at a ten-fold dilution.

Figures 6A, 6B:
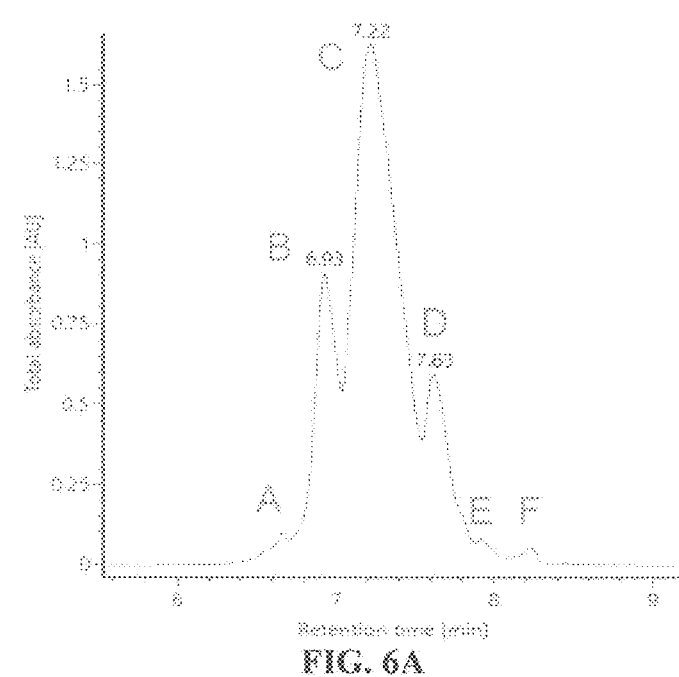
FIG. 6A is a graphical representation of the charge variants of a 1D SEC main peak fraction obtained by 2D IEX generated via a process in accordance with one or more embodiments of the disclosure.
FIG. 6B is a graphical representation of the deconvoluted spectra of the charge variants of FIG. 6A.
Figure 6C:
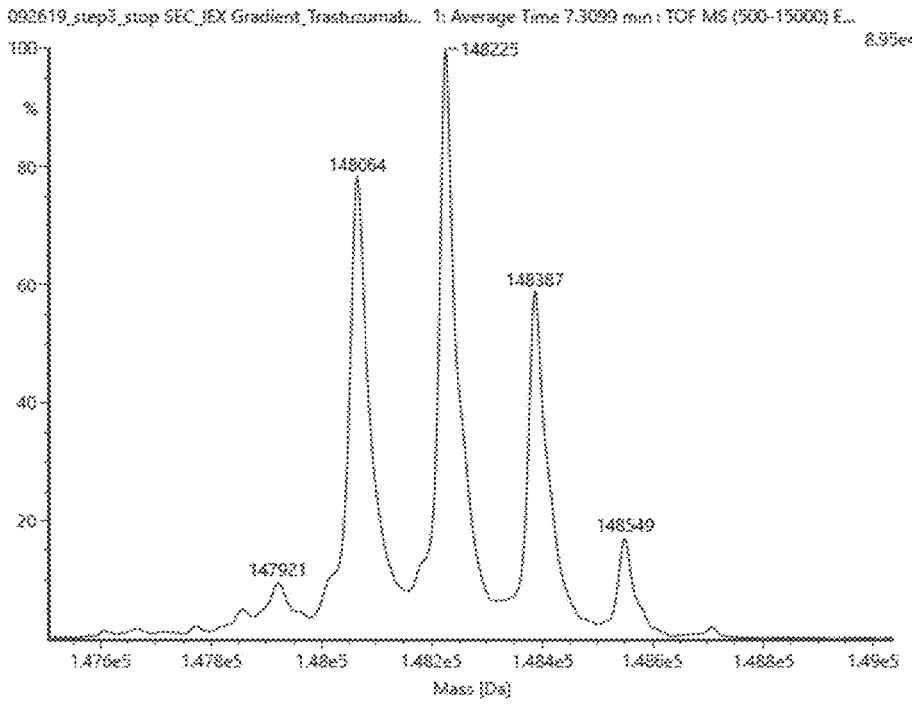
FIG. 6C is an enlarged graphical representation of the deconvoluted spectra of Peak C of FIG. 6A.

FIG. 6A depicts the charge variants of a first dimension SEC main peak fraction obtained by a second dimension IEX process at different retention times. FIG. 6B depicts the graphical representation of the deconvoluted spectra of the charge variants from FIG. 6A, where peak A is at about 6.68-6.73 minutes, peak B is at about 6.86-7.06 minutes, peak C is at about 7.21-7.41 minutes, peak D is at about 7.55-7.75 minutes, peak E is at about 7.92-8.02 minutes, and peak F is at about 8.20-8.35 minutes. FIG. 6C depicts the deconvoluted spectra of Peak C from FIG. 6A after enlargement.

Figure 7A:
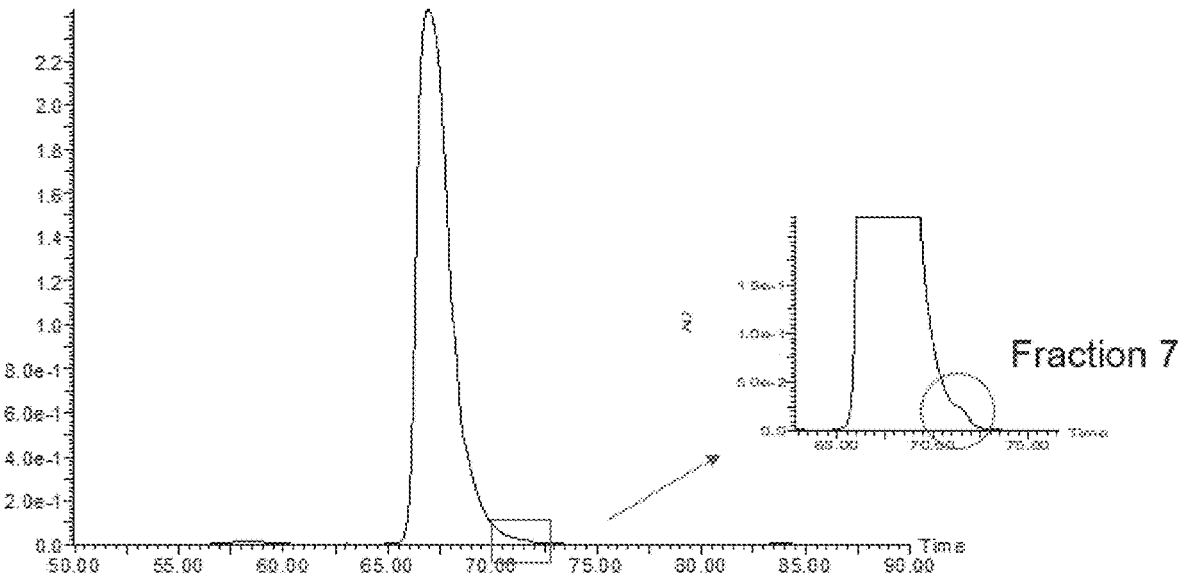
FIG. 7A is a graphical representation of a 1D SEC with a phosphate mobile phase and highlighting Fraction 7 generated via a process in accordance with one or more embodiments of the disclosure.
Figure 7B:
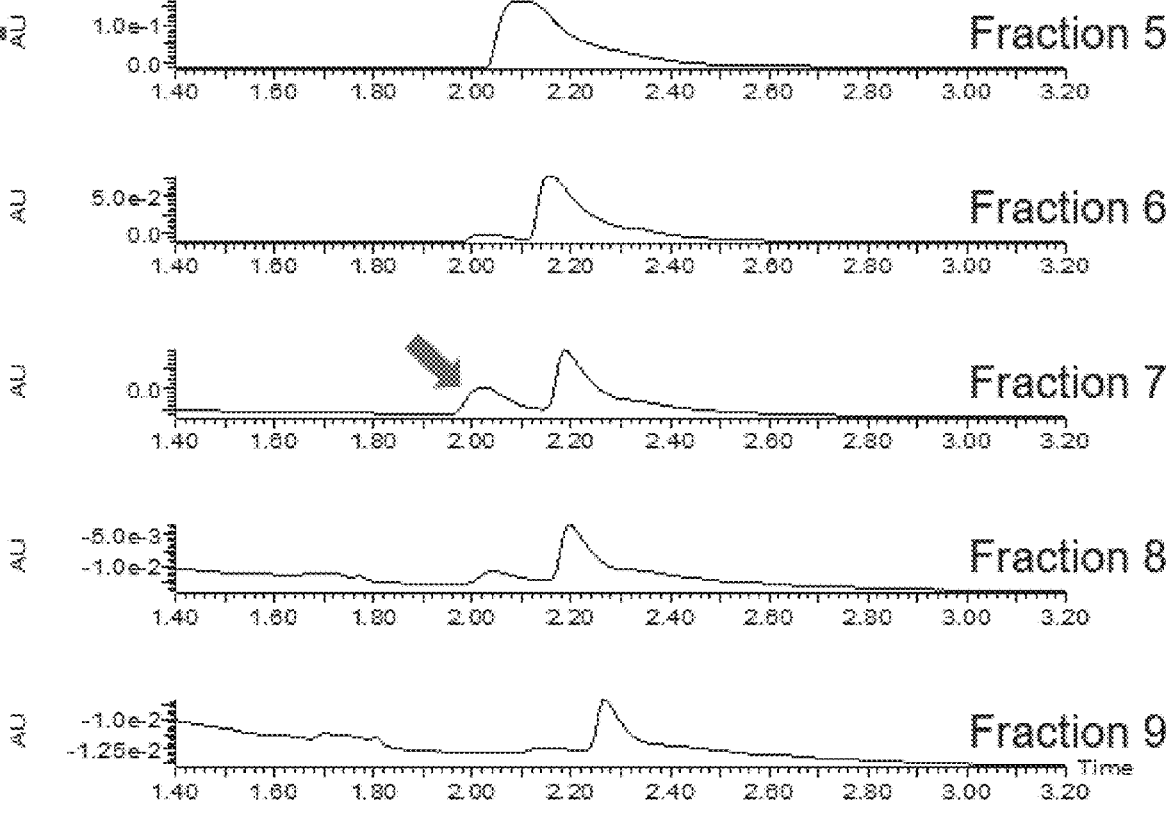
FIG. 7B is a graphical representation of a 2D RP analysis on the 1D SEC main peak fractions of FIG. 7A.

FIG. 7A depicts the results of a first dimensional process using SEC, highlighting Fraction 7. The process was carried out with a phosphate mobile phase. FIG. 7B depicts the charge variant profiling across the first dimension SEC main peak fractions by second dimension RP generated by use of the systems described herein. The graph shows the charge variances of various fractions from the first dimensional separations.

Figure 8A:
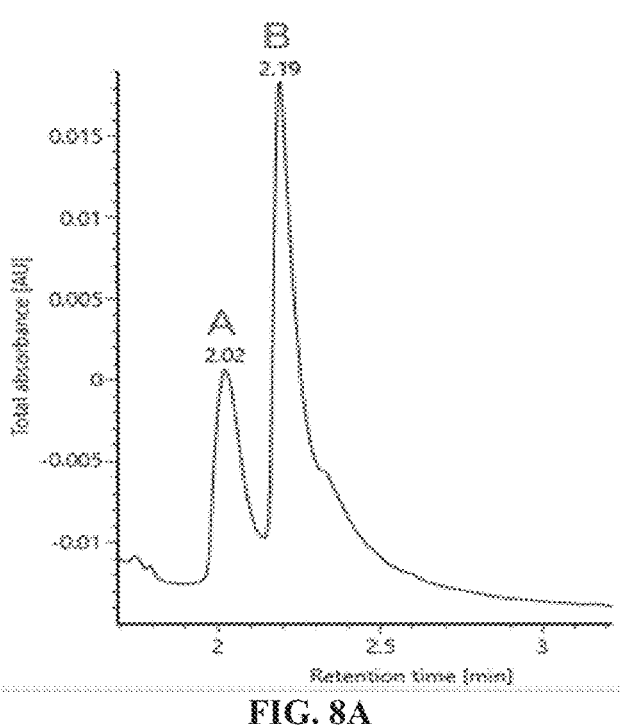
FIG. 8A is a graphical representation of a 2D RP analysis on 1D SEC main peak fractions generated via a process in accordance with one or more embodiments of the disclosure.
Figure 8B:
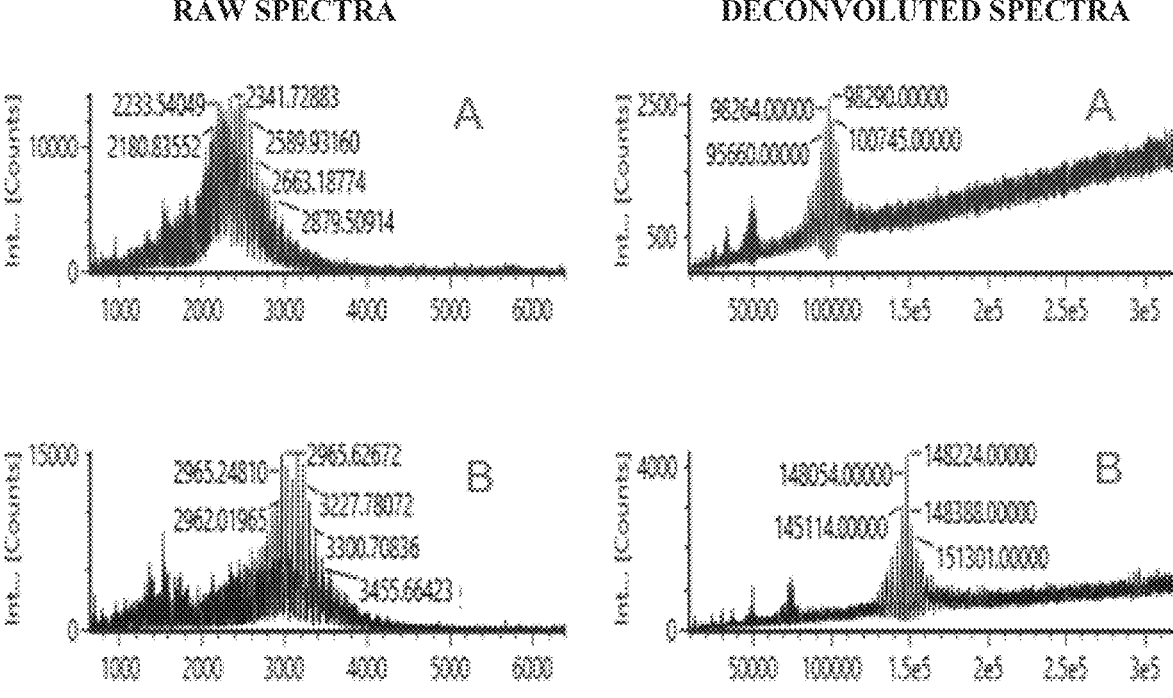
FIG. 8B is a graphical representation of the raw spectra and the deconvoluted spectra of Peaks A and B from FIG. 8A.

FIG. 8A depicts the charge variants of a first dimension SEC main peak fraction obtained by a second dimension RP process at different retention times, where peak A is at about 2.02 minutes and peak B is at about 2.19 minutes. FIG. 8B depicts the graphical representation of the raw and deconvoluted spectra of the charge variants of peaks A and B from FIG. 8A.

Having now described some illustrative embodiments of the disclosure, it should be apparent to those skilled in the art that the foregoing is merely illustrative and not limiting, having been presented by way of example only. Numerous modifications and other embodiments are within the scope of one of ordinary skill in the art and are contemplated as falling within the scope of the disclosure. In particular, although many of the examples presented herein involve specific combinations of method acts or system elements, it should be understood that those acts and those elements may be combined in other ways to accomplish the same objectives.

Furthermore, those skilled in the art should appreciate that the parameters and configurations described herein are exemplary and that actual parameters and/or configurations will depend on the specific application in which the systems and techniques of the disclosure are used. Those skilled in the art should also recognize or be able to ascertain, using no more than routine experimentation, equivalents to the specific embodiments of the disclosure. It is, therefore, to be understood that the embodiments described herein are presented by way of example only and that, within the scope of any appended claims and equivalents thereto; the disclosure may be practiced other than as specifically described.

The phraseology and terminology used herein is for the purpose of description and should not be regarded as limiting. As used herein, the term "plurality" refers to two or more items or components. The terms "comprising," "including," "carrying," "having," "containing," and "involving," whether in the written description or the claims and the like, are open-ended terms, i.e., to mean "including but not limited to." Thus, the use of such terms is meant to encompass the items listed thereafter, and equivalents thereof, as well as additional items. Only the transitional phrases "consisting of" and "consisting essentially of," are closed or semi-closed transitional phrases, respectively, with respect to any claims. Use of ordinal terms such as "first," "second," "third," and the like in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish claim elements.

What is claimed is:

1. A system for performing a two-dimensional liquid chromatography process, the system comprising:
   a first analytical subsystem comprising:

a size exclusion chromatography column as a first analytical device; and
   a first pump fluidly coupled with the size exclusion chromatography column and configured to deliver a sample to the size exclusion chromatography column;
   a second analytical subsystem comprising:
   a second analytical device different from the first analytical device; and
   a second pump fluidly coupled with the second analytical device and coupleable with a source of a diluent, wherein the second pump is configured to deliver the diluent from the source of the diluent to an eluent output from the size exclusion chromatography column and then introduce a merged flow of the diluent and the eluent to the second analytical device; and
   a mechanism configured to regulate a flow of the eluent outputted from the size exclusion chromatography column to the second analytical device without the use of a trap, the mechanism configured to stop and restart the flow of the eluent from the size exclusion chromatography column to the second analytical device for desired time periods.

2. The system of claim 1 further comprising a tee fluidly coupled with the second pump and the second analytical device and configured to receive the eluent output from the size exclusion chromatography column and the diluent from the source of diluent and merge the eluent and the diluent for introduction to the second analytical device.

3. The system of claim 1, wherein the mechanism for regulating the flow of the eluent output from the size exclusion chromatography column to the second analytical device comprises a two-position, six-port valve arrangement in fluid communication with the first analytical subsystem and the second analytical subsystem, wherein the two-position, six-port valve arrangement is configured to direct the flow of the eluent output from the size exclusion chromatography column of the first analytical subsystem to either the second analytical subsystem or an auxiliary output.

4. The system of claim 3, further comprising
   at least one of a waste receptacle, a holding tank, or an additional analytical device; and
   the auxiliary output,
   wherein the auxiliary output is fluidly coupled with the at least one of the waste receptacle, the holding tank, or the additional analytical device.

5. The system of claim 1, wherein the second analytical device comprises at least one of an ion exchange device, a hydrophobic interaction chromatography device, a purification device, a reverse phase chromatography device, or a mass spectrometer.

6. The system of claim 1, wherein the second analytical subsystem includes a third analytical device fluidly coupled to at least one of the second pump or the second analytical device.

7. The system of claim 6, wherein the third analytical device comprises at least one of an ion exchange device, a hydrophobic interaction chromatography device, a purification device, a reverse phase chromatography device, or a mass spectrometer.

8. The system of claim 6, wherein the third analytical device is oriented in parallel with the second analytical device and the second analytical subsystem further comprises a valve configured to direct the eluent of the size exclusion chromatography column to either the second analytical device or the third analytical device.

9. The system of claim 6, wherein the third analytical device is oriented in series with the second analytical device.

10. The system of claim 1, further comprising an optical detector disposed downstream of the first analytical subsystem.

11. A method of performing a two-dimensional liquid chromatography process, the method comprising the steps of:

introducing a sample to a first analytical device comprising a size exclusion chromatography column for performing a first separation of the sample;

directing a flow of an eluent output from the size exclusion chromatography column to a second analytical device for performing a second separation of the sample;

regulating the flow of the eluent output from the size exclusion chromatography column to the second analytical device without the use of a trap, wherein regulating the flow of the eluent comprises stopping the flow of the eluent from the size exclusion chromatography column to the second analytical device and restarting the flow of eluent from the size exclusion chromatography column to the second analytical device after a desired time period;

introducing a diluent to the flow of the eluent output from the size exclusion chromatography column prior to delivering the eluent and the diluent to the second analytical device; and starting the second analytical device.

12. The method of claim 11, wherein the steps of directing the flow of the eluent output from the size exclusion chromatography column and regulating the flow of the eluent to the second analytical device are carried out via a two-position, six-port valve arrangement fluidly coupled with the size exclusion chromatography column and the second analytical device, wherein a first position of the two-position, six-port valve arrangement is configured to direct the flow of the eluent output from the size exclusion chromatography column to the second analytical device and a second position of the two-position, six-port valve arrangement is configured to direct the flow of the eluent output from the size exclusion chromatography column to an auxiliary output.

13. The method of claim 11, wherein the step of introducing the diluent to the second analytical device comprises using a tee to perform an at column dilution of the flow of the eluent output from the size exclusion chromatography column into an inlet of the second analytical device.

14. The method of claim 11, wherein regulating the flow of the eluent output from the size exclusion chromatography column comprises stopping the flow of the eluent for the desired time period of at least 1 minute.

15. The method of claim 11, wherein regulating the flow of the eluent output from the size exclusion chromatography column comprises stopping the flow of the eluent for a time taken to complete the second separation with the second analytical device, wherein a protein of interest in the sample has a mass of greater than 20 kDa.

16. The method of claim 11, wherein the first and second separations of the sample are performed isocratically.

17. The method of claim 11, wherein the first and second separations of the sample are carried out with the sample at a temperature of less than 30° C.

18. The method of claim 11, wherein regulating the flow of the eluent output from the size exclusion chromatography column comprises stopping or directing the flow of the eluent to waste for the desired time period of after a first desired fraction of the sample has been directed to the second analytical device.

19. The method of claim 18 further comprising the step of restarting the flow of the eluent output from the size exclusion chromatography column to direct a next desired fraction of the sample to the second analytical device after completion of a separation with the second analytical device for the first desired fraction of the sample.

20. The method of claim 11 further comprising the step of directing a flow of an eluent output from the second analytical device to a third analytical device.

21. The method of claim 11, wherein the step of introducing the sample comprises injecting multiple samples into the size exclusion chromatography column.

22. The method of claim 11, wherein the step of regulating the flow of the eluent output from the size exclusion chromatography column is carried out without holding the eluent output from the size exclusion chromatography column.

* * * * *